United States Patent
Mathur et al.

(10) Patent No.: US 6,359,128 B1
(45) Date of Patent: Mar. 19, 2002

(54) FREE-FLOWING FLAKES OF VINYL CAPROLACTAM MONOMER AND PROCESS FOR MAKING SAME

(75) Inventors: Arvind M. Mathur, Wayne; James A. Dougherty, Kinnelon; Philip F. Wolf, Bridgewater, all of NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/618,395

(22) Filed: Jul. 18, 2000

(51) Int. Cl.[7] .................. C07D 223/10; C07D 201/00; C07D 201/16; C08F 2/46
(52) U.S. Cl. ................ 540/485; 540/532; 540/535; 540/540; 522/167; 526/264
(58) Field of Search .................. 522/167; 526/264; 540/485, 532, 533, 540

(56) References Cited

U.S. PATENT DOCUMENTS

| | | | |
|---|---|---|---|
| 4,319,811 A | * | 3/1982 | Tu et al. |
| 4,988,742 A | * | 1/1991 | Moon et al. |
| 5,037,620 A | * | 8/1991 | Perrone |
| 5,468,820 A | * | 11/1995 | Dougherty et al. |
| 5,534,564 A | * | 7/1996 | Zhong et al. |
| 5,852,202 A | * | 12/1998 | Prasad et al. |

* cited by examiner

Primary Examiner—Susan W. Berman
(74) Attorney, Agent, or Firm—Walter Katz; William J. Davis; Marilyn J. Maue

(57) ABSTRACT

Free-flowing flakes of vinyl caprolactam monomer usable below its melting point of 34° C. without developing coloration.

1 Claim, 1 Drawing Sheet

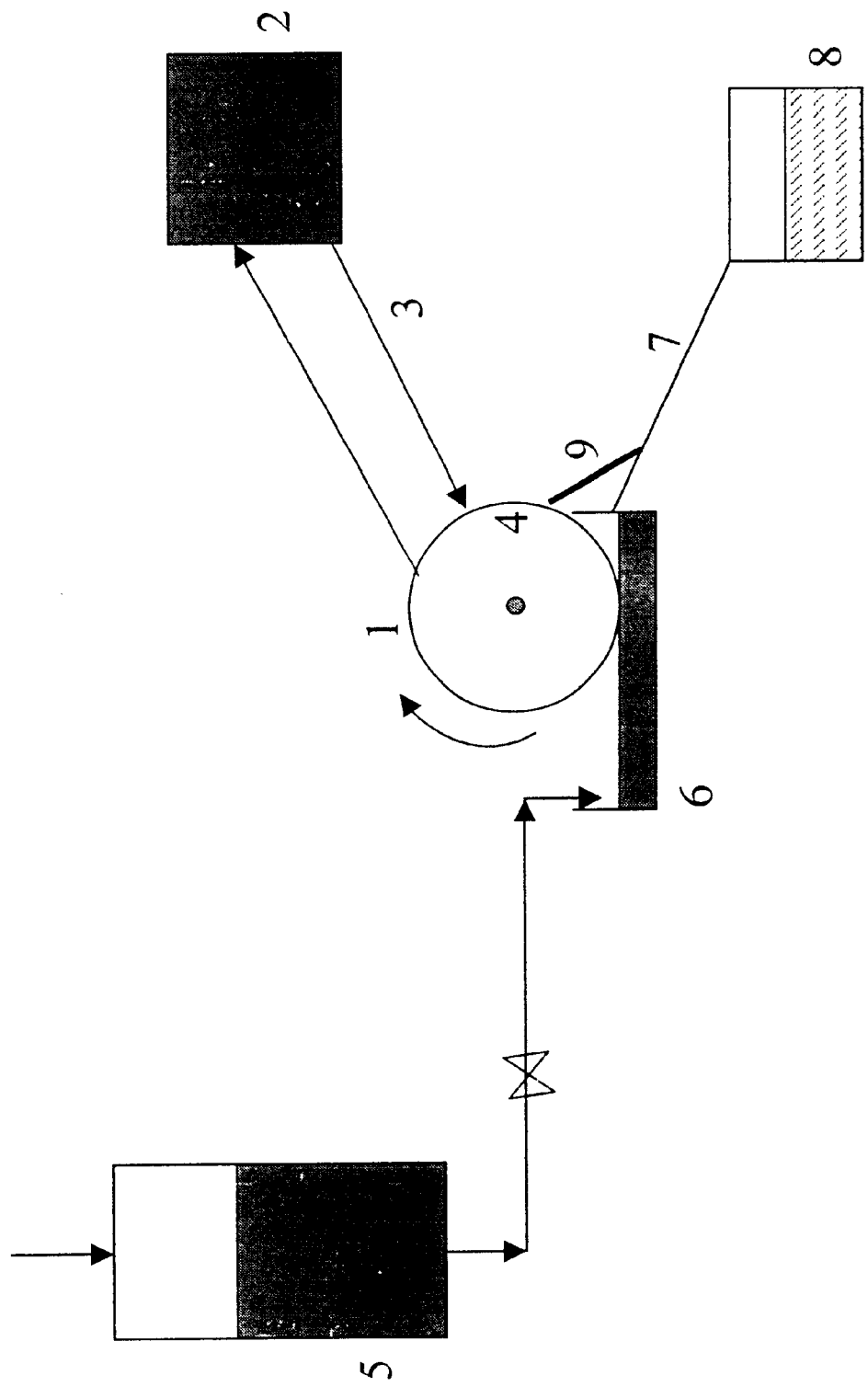
FIGURE

FREE-FLOWING FLAKES OF VINYL CAPROLACTAM MONOMER AND PROCESS FOR MAKING SAME

BACKGROUND OF THE INVENTION

1. Field of the Invention

This invention relates to vinyl caprolactam monomer (V-Cap), and, more particularly to free-flowing flakes of such monomer which is usable below its melting point of 34° C. without developing coloration, to coating and adhesive formulations thereof, and to cured, optically clear coatings thereof.

2. Description of the Prior Art

Vinyl caprolactam monomer presents a challenge in terms of handling and formulation because it is a crystalline solid at room temperature (m.p. 34° C.). The monomer is usually stabilized by an amine that prevents homopolymerization during storage. However, the amine stabilizer imparts color when the monomer is stored for an extended period of time at room temperature or for a short period at an elevated temperature. The color of the monomer also increases dramatically when stored above its melting point.

Vinyl caprolactam also exhibits an interesting phenomenon known as "super-cooling", which allows it to exist as a liquid below its melting point under certain conditions. Two factors that contribute to super-cooling are the lack of crystallization sites or "seeds" and an infinitesimally slow cooling rate. These conditions, however, are almost impossible to achieve in an industrial environment in the containers used for drumming. Hence, vinyl caprolactam users are forced to melt the monomer before subsequent handling. This melting step also increases the color of the material due to chemical reactions attributed to the amine stabilizer and trace impurities in the monomer.

Accordingly, it is desired to provide vinyl caprolactam in a form that is easy to handle, does not require energy-intensive melting before use, and that does not acquire a colorant during handling or storage.

BRIEF DESCRIPTION OF THE DRAWING

The FIGURE is a schematic illustration of the process of the invention.

SUMMARY OF THE INVENTION

What is described herein are free-flowing flakes of vinyl caprolactam monomer and storable below its melting point of 34° C. without developing coloration.

The invention herein also includes coating and adhesive formulations incorporating such monomer flakes, as for example, UV or E-beam curable coating formulations.

Another feature of the invention is the provision of a process for producing such free-flowing flakes of vinyl caprolactam monomer which includes the steps of (a) applying liquid or molten vinyl caprolactam monomer to a drum surface rotatable at a predetermined speed, (b) indirectly maintaining said surface at a temperature below the melting point of said monomer (<34° C.), cooling said liquid or molten vinyl caprolactam monomer on said surface to solidify said monomer, and then (c) continuously scraping said solid monomer from said surface to form the desired free-flowing flakes of said monomer.

In a suitable embodiment of the invention, the drum surface is maintained at about 5° C. and is spun at about 2 rpm, and freshly distilled liquid vinyl caprolactam monomer is applied in step (a). Alternatively, molten vinyl caprolactam may be fed directly from its production facility thereby not requiring an additional melting step before flaking.

DETAILED DESCRIPTION OF THE INVENTION

The feedstock herein is freshly distilled V-Cap monomer that has a very low initial color (<80 APHA). This material may be drum material that is melted in a controlled fashion to obtain the required initial APHA color, or preferably, V-Cap that is fed directly from a V-Cap distillation unit after addition of the amine stabilizer. Referring now to the FIGURE, a suitable flaking equipment is described schematically which includes a horizontal drum flaker 1 having the following features: (a) the ability to vary its drum speed, (b) a temperature control unit 2 attached to the drum to circulate a cooling liquid 3 on the inside 4 of the drum at the desired temperature, (c) a feeding apparatus 5 including a dip-pan 6 with means thereon to control the temperature of the pan, (d) a molten V-Cap feeding system that maintains a desired level of V-Cap in the pan, and (e) a collection chute 7 designed to collect flaked product 8 that is scraped off the drum by scrapper 9.

The following examples describe some operating conditions, quality of flakes produced, and the advantages of this process in terms of producing low color V-Cap flakes.

EXAMPLE 1

The flaking apparatus includes a drum flaker as shown in the FIGURE, which is equipped with a circulating bath with the capability of maintaining drum temperatures between −5 and +70° C. The dip pan attached to the flaker is hooked up to a circulating bath to maintain the pan at a temperature of 38° C. in order to maintain and feed V-Cap in a molten state. A jacketed flask under nitrogen pressure was connected to the dip-pan. The temperature of the flask was also maintained at 38° C. by connecting it to the same circulating bath that was used for the dip-pan. A valve in the dip pan feed line was used to maintain a constant level of V-Cap in the dip-pan. The nitrogen pressure in the sealed flask was kept between 10–15 psig which was sufficient to feed V-Cap into the dip pan. A polyethylene-lined chute was used to collect the flakes coming off the blade into a receiving container. A vapor collection hood was attached to the top of the drum assembly to ensure a minimum exposure to V-Cap during flaking.

Low color V-Cap was used as the feed. The drum flaker was operated at a speed of 2.1 rpm, and with the internal drum temperature was maintained at 18° C. Free-flowing flakes of V-Cap were collected in the receiver. This flaked product when melted exhibited a negligible increase in color when compared to the starting material.

EXAMPLE 2

The procedure of Example 1 was followed using V-Cap as a frozen solid which was melted under controlled conditions to limit color development during melting, and flaked immediately after melting. No significant color was generated during the flaking process; the color of the flaked material was substantially identical to the color of the starting material. For example, at an the initial color of the melted V-Cap of 225 APHA, light straw color flakes were obtained, which, when melted, exhibited a color of 253 APHA.

EXAMPLE 3

The procedure of Example 1 was followed to provide freshly-distilled and stabilized V-Cap that was obtained directly as a liquid feed from the distillation process. The initial color of the molten V-Cap was 8 APHA which is essentially water-white. White flakes also were obtained which when melted exhibited a color of only 14 APHA, which is indistinguishable by the naked eye in monomer form or in a formulation from an APHA value of 8.

EXAMPLE 4

The procedure of Example 1 was followed using an internal drum temperature of 5° C. Larger flakes with better integrity were obtained; the flake dimensions were about 1 mm thick and <1 mm round.

EXAMPLE 5

The monomer flakes obtained in Example 3 were used in a UV-curable abrasion resistant coating formulation. The flaked material was easy to handle in preparation of such formulation, and did not require a melting step thereby resulting in substantial energy savings. The resultant formulation and its cured coating do not exhibit any color. In contrast, solid V-Cap monomer gave a highly colored product.

While the invention has been described with particular reference to drum flaker for obtaining the free-flowing V-Cap flakes, it will be understood that belt flakers, prilling towers and other such apparatus may be used as well. Similarly, while the flake form is described as a preferred embodiment of the invention, other related free-flowing solid forms of the material, such as prills and sheets, which may be used as such or comminuted into smaller units, also may be obtained herein and are to be considered within the purview of this invention.

What is claimed is:

1. A process for producing free-flowing flakes of vinyl caprolactam monomer having substantially no visible color which comprises (a) applying liquid or molten vinyl caprolactam monomer under pressure to a drum surface rotatable at a predetermined speed, (b) indirectly maintaining said surface at a temperature below the melting point of 34° C. of said monomer, cooling said liquid or molten vinyl caprolactam monomer on said surface to solidify said monomer, and (c) continuously scraping said solid monomer from said surface to form the desired free-flowing flakes of said monomer.

* * * * *